United States Patent [19]

Yamanishi

[11] 4,236,826
[45] Dec. 2, 1980

[54] APPARATUS FOR OPTICALLY MEASURING A PROPERTY OF AN OBJECT

[75] Inventor: Akio Yamanishi, Tondabayashi, Japan

[73] Assignee: Minolta Camera Kabushiki Kaisha, Osaka, Japan

[21] Appl. No.: 16,561

[22] Filed: Mar. 1, 1979

[30] Foreign Application Priority Data

Mar. 7, 1978 [JP] Japan .................................. 53/26202

[51] Int. Cl.³ ........................................... G01N 21/01
[52] U.S. Cl. .................................................... 356/432
[58] Field of Search ............... 356/223, 442, 443, 444, 356/438; 364/857; 354/20

[56] References Cited

U.S. PATENT DOCUMENTS

| | | | |
|---|---|---|---|
| 1,167,045 | 1/1916 | Cade et al. | 356/438 |
| 3,528,749 | 9/1970 | Bowker | 356/443 X |
| 3,994,601 | 11/1976 | Brugger | 356/438 |

FOREIGN PATENT DOCUMENTS

48-11347  3/1973  Japan .

*Primary Examiner*—John K. Corbin
*Assistant Examiner*—Bruce Arnold
*Attorney, Agent, or Firm*—Jackson, Jones & Price

[57] ABSTRACT

An apparatus for measuring an optical property of an object such as its optical density, is disclosed. The apparatus comprises a light flash source, a photodiode coupled to a current-voltage transducer, a reference voltage source, a voltage comparator for comparing the reference voltage and voltage of the transducer, and a clock pulse generator and pulse counter triggered by the light flash source. The comparator compares the voltage from the transducer and the reference source, and disables the counter when the transducer voltage level drops below the reference voltage level. The apparatus relies upon the fact that the intensity of light emitted by the light source decays as a function of time, including a region where the intensity decays in an exponential function of time. By appropriate selection of the apparatus component parameters, the apparatus will produce a data response equal to the optical density without the need for additional logarithmic conversion circuitry.

Additional novel features and improvements are disclosed.

18 Claims, 9 Drawing Figures

APPARATUS FOR OPTICALLY MEASURING A PROPERTY OF AN OBJECT

BACKGROUND OF THE INVENTION

1. Field of the Invention

The present invention relates to an instrument for optically measuring a property of an object by means of photoelectrically receiving the output of a light source transmitted through or reflected by the object, the obtained photoelectric signal being utilized as information concerning the property of the object under inspection.

2. Description of the Prior Art

As an example of an apparatus for optically measuring a property of an object, the densitometer may be mentioned. The densitometer is an instrument for measuring optical density of an object by means of projecting a light toward the object, photoelectrically receiving the light transmitted through, or reflected by the object, and processing the obtained electric signal. In the above signal processing step of the densitometer, some complex device including logarithmic conversion means is generally required since the optical density is defined in relation with the logarithm of the obtained electric signal.

One type of densitometer known in the prior art, and disclosed in Japanese utility model publication No. 48-11347, comprises a circuit means for producing a voltage output which decays from a standard level in an exponential function of time t, means for measuring the light of a light source by way of an object to produce an output of a stationary level commensurate with the measured intensity of light, and means for counting time T between the initiation of decay of the voltage output and the attainment of the stationary level by the decaying voltage output.

In the case of the above densitometer, the circuit means for producing a decaying voltage output corresponds to the logarithmic conversion means.

SUMMARY OF THE INVENTION

An object of the present invention is to provide a novel and useful type of apparatus for optically measuring a property of an object.

Another object of the present invention is to provide an apparatus of the above mentioned type of a simplified construction.

Still another object of the present invention is to provide an apparatus of the above mentioned type which is capable of logarithmic conversion without the need of additional specific logarithmic conversion circuitry or signal processing means.

A further object of the present invention is to provide an apparatus of the above mentioned type in a compact size.

Still another object of the present invention is to provide an apparatus of the above mentioned type which is capable of utilizing a flash light source without providing any integrating means which would be required in the light receiving circuit of a conventional apparatus using a flash light source.

An additional object of the present invention is to provide an apparatus of the above mentioned type having a wide dynamic range of measurement.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

DETAILED DESCRIPTION OF THE PREFERRED EMBODIMENTS

The following description is provided to enable any person skilled in the optical measurement art to make and use the present invention and sets forth the best modes contemplated by the inventor in carrying out his invention. Various modifications to the disclosed embodiments, however, will be readily apparent to those skilled in the art, and still embrace the generic principles of the present invention disclosed herein with reference to specific embodiments.

Figure 1:
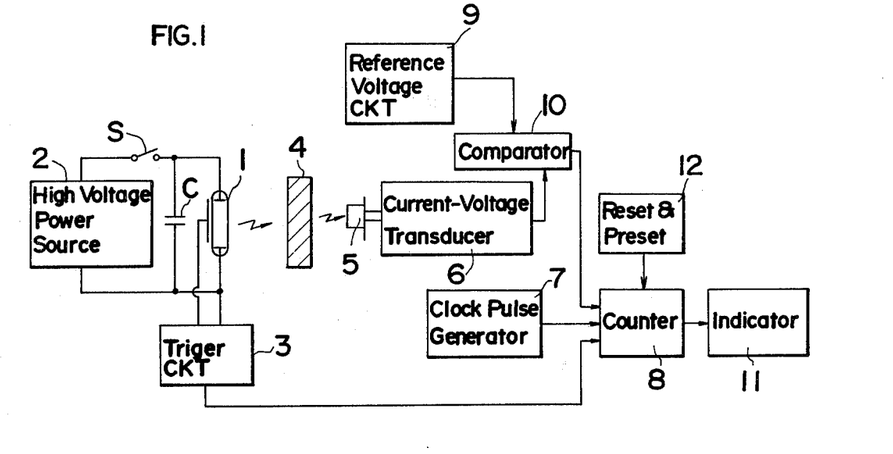
FIG. 1 is a block diagram of a first embodiment of the present invention.

The present invention will now be described in greater detail in terms of its preferred embodiments. In FIG. 1, there is illustrated a block diagram of an embodiment of the present invention, which is constructed as a densitometer and shows the principles of the present invention. A xenon flashtube 1 or the like is used as a source of light, which produces a flash of light. When a main switch S is closed, a capacitor C is charged from a high voltage power supply 2. Charge on the capacitor C is discharged through the flashtube 1 in response to a trigger signal from a trigger circuit 3, whereby the flashtube 1 releases a flash of light as original light for a measuring instrument. These components constitute a light source device.

An object of interest to be measured is labeled 4 and light emitted from the flashtube and transmitted through the object 4 impinges finally upon a photoreceptive element 5 such as a photodiode having a quick response. Current develops from the photoreceptive element 5 in proportion to quantity of the incident light and then is converted through a current-voltage transducer into a voltage signal which varies as a function of variation in quantity of the incident light. A clock pulse generator 7 produces a train of clock pulses. A counter 8 starts counting the clock pulses in synchronization with the trigger signal from the trigger circuit 3. Counter 8 may be presetable and performs additions or subtractions selectively; an example is a presetable up-down binary counter. A reference voltage generator 9 provides a given reference voltage. A comparator 10 compares the voltage signal from the transducer 6 with the given reference voltage from the generator 9 and, when the voltage signal from transducer 6 is attenuated and becomes lower than the reference voltage level, it prevents the counter 8 from counting the clock pulses. There are further provided a count indicator 11 and a reset and preset means 12 for the counter 8.

Figure 2:
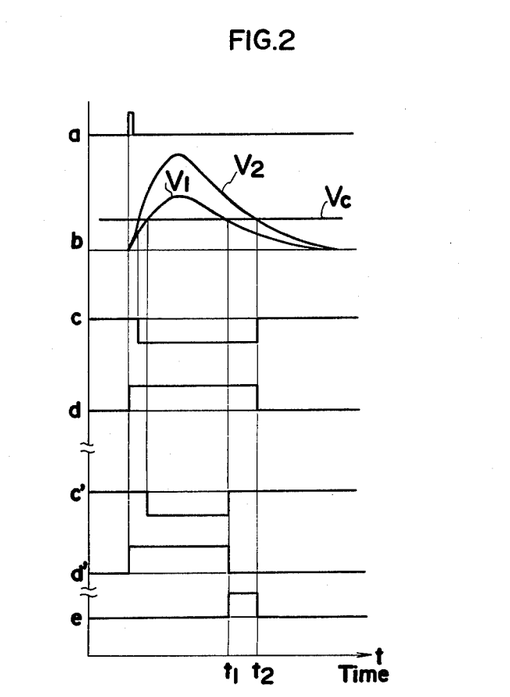
FIG. 2 is a time chart explaining the function of the first embodiment.

The illustrated embodiment will operate in the following manner. The flashtube 1 is first enabled to produce a flash of light under a standardized circumstance that no object 4 is disposed in an optical path between the flashtube 1 and the photoreceptive element 5. FIG. 2($a$) depicts the timing of the trigger signal for triggering the flashing. At the same time, the counter 8 starts counting the clock pulses as seen from FIG. 2($d$). It will be noted that the counter performs addition at this time. FIG. 2($b$) shows the relationship between the signal voltage $V_2$ from the transducer 6 and the reference voltage $V_c$ from the generator 9. Since the signal voltage $V_2$ varies in proportion to variations in quantity of light emitted from the flashtube 1 and also to variations in quantity of light received by the photoreceptive element 5, the signal voltage $V_2$ rises sharply up to a peak after the triggering operation and then falls progressively with time. FIG. 2($c$) shows the output of the comparator indicating that the comparator output is low while the signal voltage $V_2$ is higher than the reference voltage $V_c$. It is apparent from FIG. 2($d$) that the counter 8 discontinues counting the clock pulses when the output of the comparator 10 changes from low to high at $t_2$. In this way, a preliminary reference measurement with no object disposed in place is accomplishing and hence the reference measurement with reference light is finished. As a result, the counter holds the number of the pulses corresponding to the period of time denoted by FIG. 2($d$). This number of pulses is utilized as a reference standard of measurement. The object of interest 4 is next located within the optical path as shown in FIG. 1 for the main measurement wherein the flashtube 1 is enabled to emit another flash of light as in the preliminary measurement. It is clear from FIG. 2($b$) that the signal voltage varies in time sequence as represented by the curve $V_1$ since quantity of light incident upon the photoreceptive element 5 is reduced as a function of the light transmission factor of the object of interest.

The counter starts counting the clock pulses as seen from FIG. 2($d'$) when the flashtube 1 is triggered. In this case, the counter performs subtraction. Therefore, the number of the pulses contained within the counter 8 obtained by the preliminary reference measurement is reduced progressively as the counter 8 counts the pulses. The output of the comparator as depicted in FIG. 2($c'$) is inverted from low to high at time $t_1$. When this occurs, the counter 8 stops the subtractive pulse count and thus retains the number of pulses corresponding to the period from $t_1$ to $t_2$ as shown in FIG. 2($e$). This remainder pulse count is visually indicated as measured data on the indicator 11.

The findings of the reference light or preliminary measurement remain unchanged as long as the high voltage power supply 2 is voltage-stabilized and the quantity of light emitted from the flashtube 1 is identical at every flash. Therefore, once the necessary reference value is measured and evaluated by one preliminary measurement reference, this value can be preset in the counter 8 through the reset and preset means 12 to eliminate the need to repeat the reference measurement, and facilitate the succeeding plurality of main measurements.

As long as the number of the pulses during the period as denoted by FIG. 2($d$) and 2($d'$) are obtainable, the number of the pulses during the period from $t_2$ and $t_1$ can be easily evaluated through manual subtraction. Thus, the counter 8 may be a simple binary counter in place of the above mentioned presetable up-down counter. In this case the findings of the reference light measurement and the main measurement can be calculated later on.

It is obvious that the counting operation may begin at any time as long as it is guaranteed that the counting would begin at the same point in time at every measurement.

Figure 3:
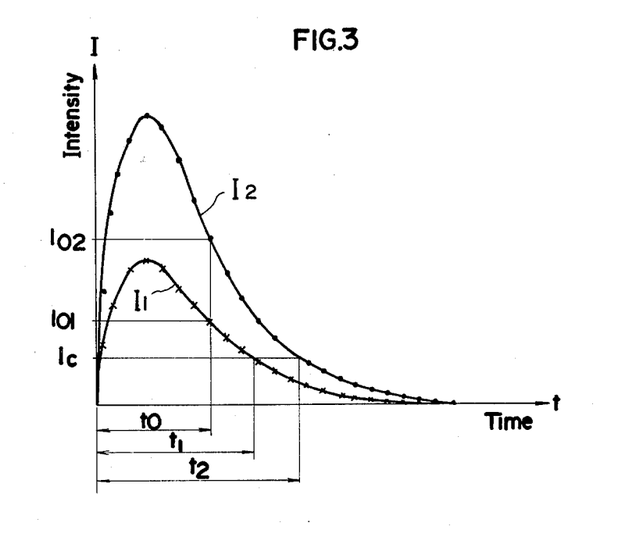
FIGS. 3 and 4 are graphical plots explaining the operation of the present invention.
Figure 4:
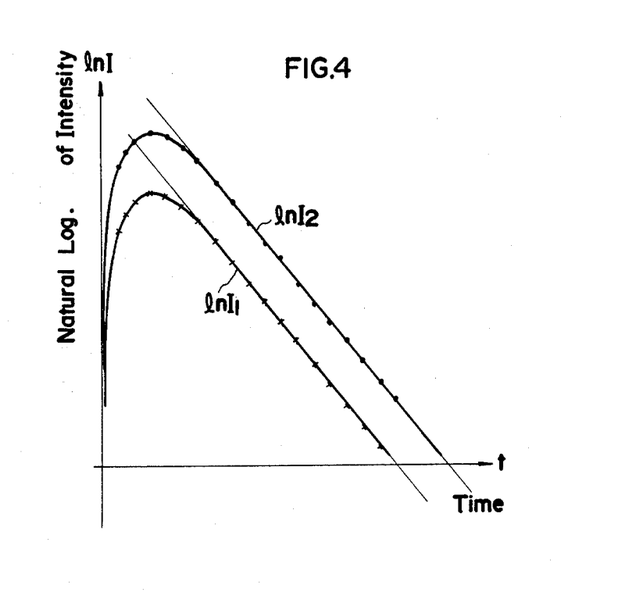

The measurements with logarithm conversion according to the present invention will be discussed theoretically. The graph in FIG. 3 represents actually measured variations in intensity of light emitted from the xenon flashtube as a function of time, wherein $I_2$ denotes intensity of received light when the emitted light is incident directly upon the photoreceptive element 5 (with no object in the light path) in the preliminary measurement and $I_1$ denotes intensity of received light when the object with transmission factor T is located in front of the photoreceptive element in the main measurement. FIG. 4 is a version of FIG. 3 with the ordinate graduated by natural logarithms of intensity of received light, indicating that there is definitely a linearity region in the attenuation of intensity of received light. In other words, this provides the actual proof that the intensity of emitted light attenuates as an exponential function of time within an optimal segment of the attenuation region as seen from the intensity curve of FIG. 3.

Assume now that in FIG. 3 intensities of received light are labeled $I_{01}$ and $I_{02}$ at the particular point within the region where intensity of emitted light attenuates as an exponential function of time. Within this region, variations in intensities $I_1$ and $I_2$ of received light as a function of time can be represented as below:

$$I_1 = I_{01} \cdot e^{-(t-t_0)/\tau} \quad (1)$$

$$I_2 = I_{02} \cdot e^{-(t-t_0)\tau} \quad (2)$$

wherein $\tau$ is a time constant. If the voltage from the high voltage power supply 2 is unchanged during the reference light measurement and the main measurement, intensity of emitted light is therefore uniform so that the following relationship is satisfied between the intensities of received light in the reference and main measurements.

$$I_{01} = T \cdot I_{02} \quad (3)$$

On the other hand, a predetermined level of intensity of received light is labeled $I_c$ in FIG. 3. Provided that $I_1$ and $I_2$ become equal to the level of $I_c$ at $t_1$ and $t_2$, respectively due to attenuation of the intensity of emitted light, the following relationships can be obtained from formulas 1 and 2:

$$I_c = I_{01} \cdot e^{-(t_1 - t_0)/\tau} \quad (4)$$

$$I_c = I_{02} \cdot e^{-(t_2 - t_0)/\tau} \quad (5)$$

From the formulas (4) and (5), $$\frac{I_{01}}{I_{02}} = \frac{e^{-(t_2 - t_0)/\tau}}{e^{-(t_1 - t_0)/\tau}} = e^{-(t_2 - t_1)/\tau} \quad (6)$$

In other words, the period of time from $t_1$ to $t_2$ can be expressed:

$$t_2 - t_1 = -\tau \cdot \ln \frac{I_{01}}{I_{02}} = -\tau \cdot \log \frac{I_{01}}{I_{02}} \cdot \frac{1}{\log e} \quad (7)$$
$$= -\log \frac{I_{01}}{I_{02}} \cdot \frac{\tau}{\log e}$$

Since in the formula (7) $\tau$ is the time constant fixed by the capacitance of the capacitor C and the type of flashtube used, and log e is a constant value, it is concluded that $(t_2-t_1)$ is proportional to common logarithm of $I_{01}/I_{02}$. In other words, the present invention is able to obtain directly a quantity proportional to the logarithm of a ratio of intensity $I_{01}$ of measured light to intensity $I_{02}$ of reference light by measuring the period of time from $t_1$ to $t_2$.

In measuring optical density, the relationship between the optical density D and the transmission factor T is defined as follows:

$$D = \log 1/t \quad (8)$$

The formula (7) can be rewritten from the formulas (3) and (8):

$$t_2 - t_1 = D \cdot \frac{\tau}{\log e} \quad (9)$$

Thus, a quantity proportional to the density D can be evaluated directly by measuring $(t_2-t_1)$.

The foregoing discussion has been made in terms of intensity I of received light. It is understood that the quantity proportional to the density D is available from the embodiment of FIG. 1 by correlating the signal voltages $V_1$, $V_2$ and the reference voltage $V_c$ of FIG. 2 with the intensities $I_1$, $I_2$ of received light and the intensity $I_c$ of reference received light, respectively, since the current-voltage transducer 6 of FIG. 1 provides an output voltage which varies in proportion with variations in intensity of received light. The output data at indicator 11 are represented by the number of the pulses counted by the embodiment of FIG. 1 so that the number of the pulses is made equal to the density D by adjusting the pulse period of the clock pulses in line with the proportional constant $\tau/\log e$ defined in the formula (9), thereby eliminating the need of a particular calculation circuit for displaying purposes.

Figure 5:
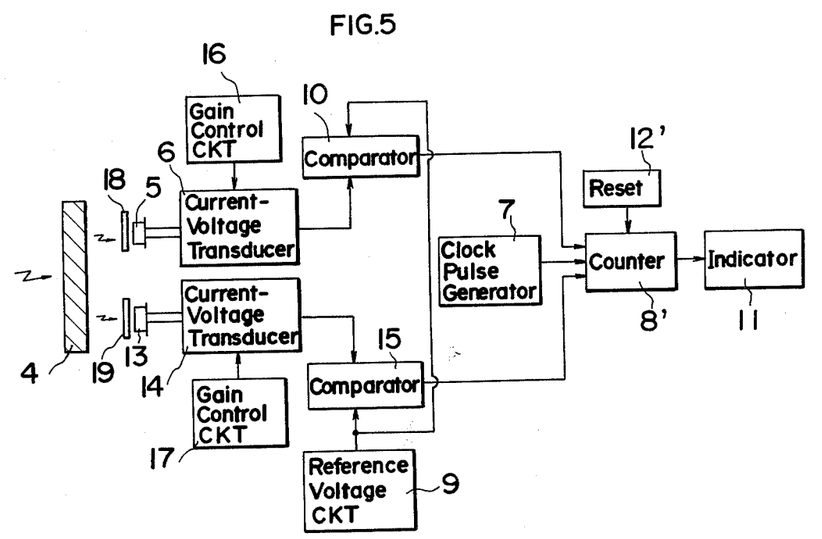
FIG. 5 is a block diagram of a second embodiment of the present invention.
Figure 6:
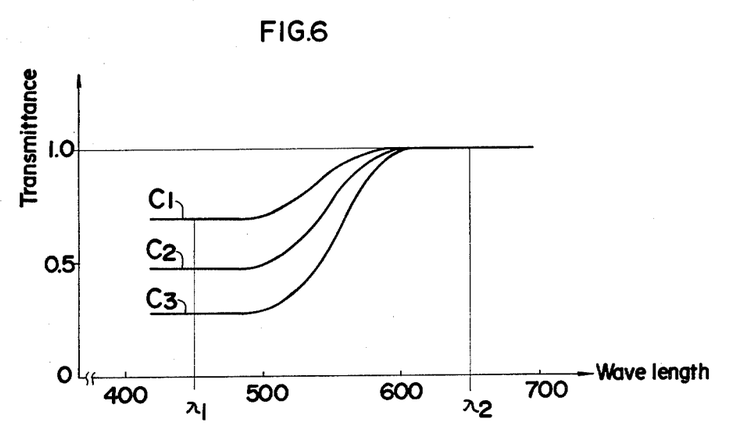
FIG. 6 is a graphical plot relating to the function of the second embodiment.
Figure 7:
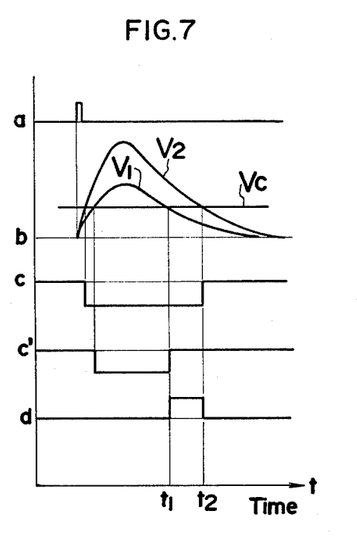
FIG. 7 is a time chart explaining the function of the second embodiment.

FIG. 5 illustrates another embodiment of the present invention wherein the reference measurement and the main measurement are carried out simultaneously. The components in the circuit of FIG. 5 are given the same numbers as in FIG. 1. The light source device shown in FIG. 1 is omitted for simplicity. It is clear from FIG. 5 that this embodiment includes a pair of combinations of the photoreceptive element 5, the current-voltage transducer circuit 6 and the comparator 10 as in FIG. 1. A second photoreceptive element is labeled 13, a second current-voltage transducer is labeled 14 and a second comparator is labeled 15. The reference voltage generator 9 is common to the comparators 10 and 15. Gain adjusting means 16 and 17 are provided to establish a proper relative gain for the output voltages of the current-voltage transducers 6 and 14. Filters 18 and 19 are disposed in front of the photoreceptive elements 5 and 13, with filter 18 for transmission of light of wavelength $\lambda_1$ as shown in FIG. 6 and filter 19 for transmission of light of wavelength $\lambda_2$. The curves $C_1$, $C_2$ and $C_3$ in FIG. 6 show the transmission factor vs. wavelength characteristics of three objects having different optical densities. As is seen from FIG. 6, the transmission factor with respect to light of wavelength $\lambda_2$ is always constant without regard to the density of the object so that the quantity of light received through the object varies without regard to the object. This implies that the photoreceptive element 13 is responsive to light passing through the object and receives substantially the reference light at wavelength $\lambda_2$. The curve $V_2$ in FIG. 7 depicts variations in output signal voltage from the current-voltage transducer 14. As is clear from FIG. 6, the quantity of light received by the photoreceptive element 5 varies in different ways according to the object to be measured. The curve $V_1$ in FIG. 7 traces variations in the output signal voltage from the current-voltage transducer 6 connected to the photoreceptive element 5. FIGS. 7(C) and 7(C') indicates that the output of the comparator 15 changes from low to high at $t_2$ whereas the counterpart comparator 10 changes from low to high at $t_1$. Attention is called to the fact that comparison between $V_1$ and $V_c$ occurs in parallel with comparison between $V_2$ and $V_c$ in this embodiment. Therefore, if the counting operation by simple counter 8' starts with the inversion of the output of the comparator 10 at $t_1$ and ends with the inversion of the output of the comparator 15 at $t_2$, then the resulting count will exactly correspond to the period from $t_1$ to $t_2$ as shown at d of FIG. 7.

As an alternate, light of the flash tube via the object may be incident upon only the photoreceptive element 5 and light from the flashtube incident directly upon the remaining photoreceptive element 13 without the wavelength selecting filters 18 and 19 as far as the relative position among the flashtube, the object, the two photoreceptive elements and the like permits. One major feature of the embodiment of FIG. 5 is that the relationship $I_{01} = T \cdot I_{02}$ is constantly maintained without any adverse effects in measuring the density D even if the quantity of emitted light varies at every flash due to variations in the power supply voltage to the flashtube. This is because the reference light measurement and the main measurement are effected through one flash of light in FIG. 5.

The FIG. 5 embodiment can be modified into a medical instrument for measuring jaundice if filter 18 is capable of transmitting light of wavelength about 460 nm at which the absorption by bilirubin is at its peak, and filter 19 is capable of transmitting light of wavelength longer than about 500 nm which is not absorbed by bilirubin.

Figure 8:
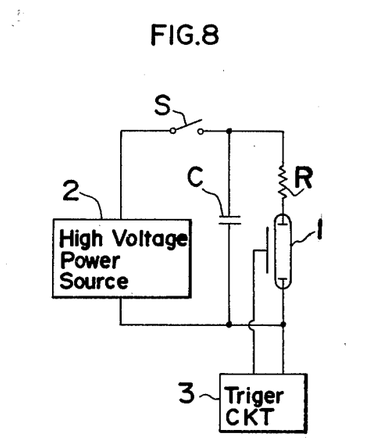
FIG. 8 is a circuit diagram showing a modification of the light source circuit of the present invention.

FIG. 8 illustrates a modification in the light source device. Pursuant to the teachings of the present invention, the greater the time constant $\tau$ with respect to attenuation of quantity of emitted light, the greater the accuracy of detecting the timing of $t_1$ and $t_2$ to minimize error in the measurements. To this end, in FIG. 8 a resistor R having substantially the same resistance (approximately 1 ohm) as the flashtube is connected in series with the flashtube 1 with the accompanying increase in the time constant $\tau$.

It is obvious that the present invention is equally applicable to a measurement device of the type wherein light emitted from the light source and reflected by the object is incident upon the photoreceptive element. Therefore, the invention may be described as an apparatus which receives light from the light source via the object.

As noted earlier, as a consequence of analysis of attentuation of the quantity of light emitted from the flashtube, the present invention relies upon the fact that quantity of emitted light attentuates as an exponential function of time. Therefore, the present invention performs the measurements with logarithmic conversion by detecting a time when the quantity of received light falls down to a preselected level. The present invention provides a novel measurement device which achieves measurements with logarithm conversion by a simple circuit construction without utilizing an integration circuit and a logarithm converter.

In addition, the present invention is very useful as a compact measurement device since a light source is implemented with the flashtube or the like to reduce a space requirement to a minimum and ensure a sufficient amount of emitted light.

Figure 9:
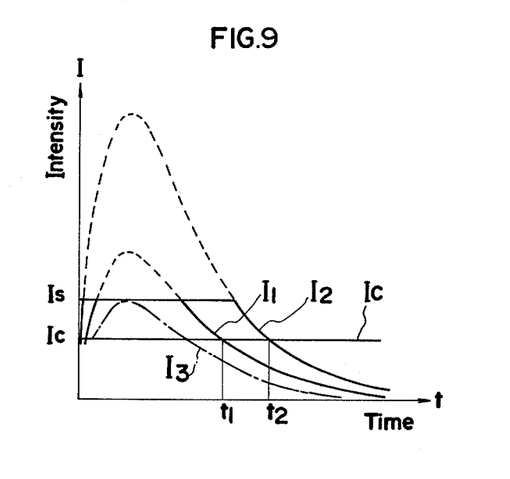
FIG. 9 is a graphical plot explaining one of the advantages of the present invention.

The following outstanding advantages can be further expected since the measurements according to the present invention take advantage of the instantaneous value which varies from time to time according to the degree of attenuation of intensity of emitted light instead of an integrated value of intensity of received light. It should be noted that the light receiving device of the present invention is not required to cover the overall range of varying intensity of received light, since it does not matter in detecting $t_1$ and $t_2$ if the light receiving device is saturated at the quantity Is of received light and thus fails to follow the change in intensity as shown in phantom in FIG. 9. In other words, this suggests that it becomes possible to employ a light source of extremely high intensity of emitted light as compared with the operating range of the light receiving device and extend the dynamic range of measurement by selecting the operating range of the light receiving device so as to cover only the necessary portion where quantity of light attenuates in the form of an exponential function. In a sharp contrast to this, it was difficult to use light stronger than denoted by the chain-dotted curve $I_3$ in FIG. 9 for measuring purposes within the prior art device wherein a light flash source was used as a source of light and data were represented by total quantity of received light and hence by an integrated value and logarithm conversion was thereafter carried out.

What is claimed is:

1. An apparatus for optically measuring a property of an object comprising:
    means for producing a flash of light, the intensity of which decays as a function of time, said function including at least a region wherein the light intensity decays in an exponential function of time;
    means for receiving light of the light producing means via the object and for producing an output which changes in response to the change in intensity of the received light;
    means for detecting a time when the output of said light receiving and output producing means reaches a predetermined level.

2. The apparatus of claim 1, wherein said means for producing a flash of light comprises an electronic flash tube.

3. The apparatus of claim 1, wherein said means for counting time is adapted to initiate the time counting in relation with the triggering of the light producing means and to terminate the time counting in relation with the signal of the generating means.

4. The apparatus of claim 3, wherein said means for counting time comprises a clock pulse generator and a counter for counting the clock pulses.

5. The apparatus of claim 4, wherein said counter is an up-down binary counter, wherein said pulses are additively counted upon a first measurement with the light path from said means for producing a flash of light to the light receiving and output producing means not influenced by the existence of the object, and are subtractively counted upon a second measurement with the light path influenced by the existence of the object.

6. The apparatus of claim 1, wherein the light receiving and output producing means comprises a pair of light receiving elements and is adapted to produce a pair of outputs each changing in response to the change in intensity of light received.

7. The apparatus of claim 6, wherein said means for generating a signal comprises a first means for generating a first signal when one of the pair of outputs reaches a predetermined level, and a second means for generating a second signal when the other of the pair of outputs reaches a predetermined level.

8. The apparatus of claim 7, wherein said means for counting time is adapted to start the time counting in response to the first signal from the first means and to terminate the time counting in response to the second signal from the second means.

9. The apparatus of claim 8, wherein said first and second light receiving elements are adapted to be responsive to light of different wavelengths from each other.

10. The apparatus of claim 8, wherein said light path from said means for producing a flash of light to one of said pair of light receiving elements is not influenced by the existence of the object and said light path from said means for producing a flash of light to the other of the pair of light receiving elements is influenced by the existence of the object.

11. The apparatus of claim 10, wherein the light receiving and output producing means further comprises a pair of filters disposed in front of the pair of light receiving elements, respectively, one of the pair of filters selectively transmitting a light of wavelength to which the property of the object is insensitive, while the other of the pair of filters selectively transmitting a light of wavelength to which the property of the object is sensitive.

12. The apparatus of claim 1, wherein said means for producing a flash of light includes means for increasing the decay time of light intensity.

13. An apparatus for measuring the optical density of an object, comprising:
    means for producing a flash of light, the intensity of which decays as a function of time, said function including at least a region wherein the light intensity decays in an exponential function of time;
    means for receiving light of the light producing means via the object to produce an output which changes in response to the change in intensity of the received light;
    timing means for determining the time differential between a first time interval from a first reference time to the time when said output voltage reaches a predetermined level when the light path from said light generating means to said light receiving means is not influenced by the object, and a second time interval from a second reference time to the time when said output voltage reaches said predetermined level when said light path is influenced by the object.

14. The apparatus of claim 13 wherein said first reference time corresponds to said second reference time.

15. The apparatus of claim 14 wherein said timing means includes means responsive to the output of the light receiving and output producing means for generating a signal when said output reaches said predetermined level, and means for counting time controlled by the signal of the generating means.

16. The apparatus of claim 15 wherein the first and second reference times are established in relation to the triggering of the light producing means.

17. The apparatus of claim 5 further comprising means for indicating the light transmissive property of the object in proportion to the time counted by said time counting means.

18. The apparatus of claim 8 further comprising means for indicating the light transmissive characteristic of the object in proportion to the time counted by said time counting means.

* * * * *

UNITED STATES PATENT AND TRADEMARK OFFICE
CERTIFICATE OF CORRECTION

PATENT NO. : 4,236,826
DATED : December 2, 1980
INVENTOR(S) : Akio Yamanishi

It is certified that error appears in the above—identified patent and that said Letters Patent is hereby corrected as shown below:

Column 5, line 21, delete "D = log 1/t" and insert
--D = log 1/T--.

Column 7, Claim 1, line 57, delete "." and insert
--which comprises means for generating a signal when the output of the light receiving and output producing means reaches a predetermined level, and means for counting time controlled by said signal.--.

Signed and Sealed this

Twenty-first Day of April 1981

[SEAL]

Attest:

RENE D. TEGTMEYER

*Attesting Officer*    *Acting Commissioner of Patents and Trademarks*